(12) United States Patent
    Syn

(10) Patent No.:   US 12,622,775 B2
(45) Date of Patent:      May 12, 2026

(54) HIATAL HERNIA REPAIR MESH WITH STARLOCK CONFIGURATION FOR HIATAL HERNIA REPAIRS AND METHODS THEREOF

(71) Applicant: SYN LLC, Lubbock, TX (US)

(72) Inventor: David Syn, Lubbock, TX (US)

(73) Assignee: SYN LLC, Lubbock, TX (US)

( * ) Notice: Subject to any disclaimer, the term of this patent is extended or adjusted under 35 U.S.C. 154(b) by 44 days.

(21) Appl. No.: 18/811,363

(22) Filed: Aug. 21, 2024

(65) Prior Publication Data

US 2026/0053613 A1   Feb. 26, 2026

(51) Int. Cl.
    *A61F 2/00*      (2006.01)
(52) U.S. Cl.
    CPC .... *A61F 2/0063* (2013.01); *A61F 2230/0021* (2013.01); *A61F 2240/001* (2013.01)
(58) Field of Classification Search
    CPC ............ A61F 2/0063; A61F 2002/0068; A61F 2002/0072; A61B 2017/00827
    See application file for complete search history.

(56) References Cited

U.S. PATENT DOCUMENTS

| | | | |
|---|---|---|---|
| 6,258,124 B1 | 7/2001 | Darios et al. | |
| 6,736,823 B2 * | 5/2004 | Darois | .................. A61F 2/0063 |
| | | | 623/23.72 |

| | | | |
|---|---|---|---|
| 2001/0049539 A1 | 12/2001 | Rehil | |
| 2007/0038232 A1 * | 2/2007 | Kraemer | ............. A61B 17/1114 |
| | | | 606/153 |
| 2013/0030339 A1 * | 1/2013 | De Gols | ............... A61F 2/0063 |
| | | | 602/41 |

OTHER PUBLICATIONS

Castelijns et al. "A collective review of biological versus synthetic mesh-reinforced cruroplasty during laparoscopic Nissen fundoplication" J Min Access Surg 2018;14:87-94 (Year: 2018).*

* cited by examiner

*Primary Examiner* — Elizabeth Houston
*Assistant Examiner* — Lindsey Bachman
(74) *Attorney, Agent, or Firm* — Whitaker Chalk Swindle & Schwartz PLLC; Juan Vasquez; Enrique Sanchez, Jr.

(57)          ABSTRACT

A hiatal hernia repair mesh with starlock configuration for providing structural reinforcement to hiatal hernia repairs and a mechanism to prevent esophageal sliding. The hiatal hernia repair mesh includes a mesh frame configured to provide structural support to a repaired hiatus when positioned against the repaired hiatus. The hiatal hernia repair mesh includes a central opening disposed within the mesh frame, configured to surround an esophagus and allow the esophagus to pass through the mesh frame. A starlock configuration is disposed around the central opening, including a plurality of flexible leaflets extending inwardly from a perimeter of the central opening. Each of the flexible leaflets is configured to allow movement of the esophagus in a first direction to allow esophageal dilation during peristalsis while providing resistance against movement of the esophagus toward a chest cavity to prevent recurrence of a hiatal hernia.

8 Claims, 6 Drawing Sheets

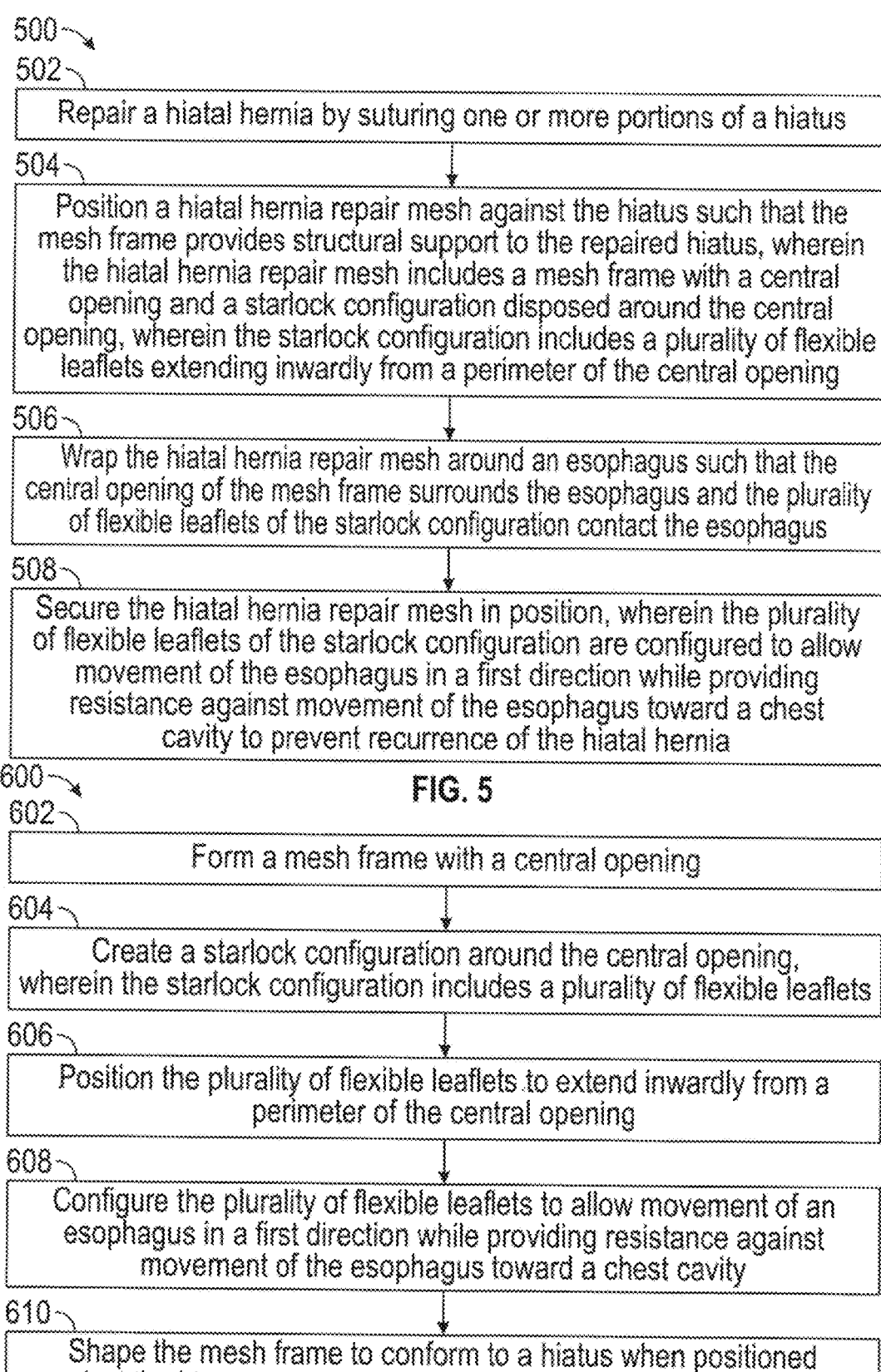

500

502

Repair a hiatal hernia by suturing one or more portions of a hiatus

504

Position a hiatal hernia repair mesh against the hiatus such that the mesh frame provides structural support to the repaired hiatus, wherein the hiatal hernia repair mesh includes a mesh frame with a central opening and a starlock configuration disposed around the central opening, wherein the starlock configuration includes a plurality of flexible leaflets extending inwardly from a perimeter of the central opening

506

Wrap the hiatal hernia repair mesh around an esophagus such that the central opening of the mesh frame surrounds the esophagus and the plurality of flexible leaflets of the starlock configuration contact the esophagus

508

Secure the hiatal hernia repair mesh in position, wherein the plurality of flexible leaflets of the starlock configuration are configured to allow movement of the esophagus in a first direction while providing resistance against movement of the esophagus toward a chest cavity to prevent recurrence of the hiatal hernia

Form a mesh frame with a central opening

604

Create a starlock configuration around the central opening, wherein the starlock configuration includes a plurality of flexible leaflets

606

Position the plurality of flexible leaflets to extend inwardly from a perimeter of the central opening

608

Configure the plurality of flexible leaflets to allow movement of an esophagus in a first direction while providing resistance against movement of the esophagus toward a chest cavity

610

Shape the mesh frame to conform to a hiatus when positioned against the hiatus, wherein the mesh frame is configured to provide structural support to a repaired hiatus

FIG. 6

HIATAL HERNIA REPAIR MESH WITH STARLOCK CONFIGURATION FOR HIATAL HERNIA REPAIRS AND METHODS THEREOF

TECHNICAL FIELD

The present disclosure relates generally to medical devices, and more particularly to a hiatal hernia repair mesh with starlock configuration for hiatal hernia repair and methods thereof.

BACKGROUND

The human digestive system is a remarkable biological mechanism that enables the conversion of food into essential energy for the body. However, this complex system can sometimes experience issues that affect its normal functioning. One such problem is the occurrence of hiatal hernias, which involve a disruption in the normal anatomy of the junction between the esophagus and the stomach.

In typical human anatomy, as illustrated in FIG. 1A, the stomach 170 is separated from the chest cavity by a muscular structure called the diaphragm 160. The esophagus 175, which is the tube that carries food from the mouth to the stomach, passes through an opening in the diaphragm known as the hiatus 165. Under normal circumstances, as shown in FIG. 1A, the hiatus 165 is adequately sized to allow only the passage of the esophagus 175. The junction of the esophagus 175 to the stomach 170, the esophagogastric or gastroesophageal junction includes the lower esophageal sphincter. This sphincter acts as a valve and, when it is positioned at the hiatus, functions normally to prevent reflux. The support structures in the area of the hiatus that correctly position the sphincter and support the gastric flap valve include the phrenoesophageal ligament 168, the gastric sling fibers 169, and the gastric clasp fibers 167.

However, in cases of hiatal hernias, as shown in FIG. 1B, this opening becomes dilated or weakened, allowing a portion of the stomach 170, and sometimes other organs, to protrude into the chest cavity as a hiatal hernia 180. The hernia direction 182 in FIG. 1B indicates the upward movement of the stomach through the enlarged hiatus 165. Additionally, in a hiatal hernia, not only is the hiatus dilated but the support structures at the hiatus, such as the phrenoesophageal ligament 168, the gastric sling fibers 169, and the gastric clasp fibers 167, are compromised causing the lower esophageal sphincter to become ineffective as it is no longer positioned properly to be supported by the hiatus and making the gastric flap valve innefective.

Typically, hiatal hernias can be classified into different types. The most common form, accounting for the vast majority of cases, is known as a type 1 or sliding hiatal hernia. In this type, the stomach intermittently slides up into the chest through the enlarged hiatus. Less common are types II, III, and IV, collectively referred to as paraesophageal hernias. These occur when a portion of the stomach and sometimes other organs push up into the chest cavity adjacent to the esophagus.

While many individuals with hiatal hernias may remain asymptomatic, those who do experience symptoms often present with issues related to chronic acid reflux, also known as gastroesophageal reflux disease (GERD). The symptoms of GERD can include heartburn, a burning sensation in the chest (particularly after eating), non-cardiac chest pain, a taste of acid in the back of the mouth, difficulty swallowing, dry cough, bad breath, nausea or vomiting, and/or other symptoms such as globus, which causes the patient to experience the sensation of having something stuck in their throat. In severe cases, persistent long-term reflux may lead to more serious complications, including an increased risk of esophageal cancer.

While hiatal hernias can affect individuals across various demographics, they are more commonly observed in older adults and individuals who are obese. In fact, the prevalence of hiatal hernias is particularly high in the bariatric population, with up to 90% of obese individuals potentially affected.

The relationship between obesity and hiatal hernias becomes even more complex when considering bariatric surgery as a treatment for obesity. For example, vertical sleeve gastrectomy, which is currently the most common form of bariatric surgery, can potentially exacerbate existing hiatal hernias or increase the risk of developing them. This is because the procedure increases pressure within the stomach, which can aggravate reflux issues and complicate hiatal hernia management in a population already prone to these problems.

Despite the high incidence of hiatal hernias in obese individuals, these hernias are not typically addressed during sleeve gastrectomy procedures. This is partly due to the lack of a standardized, effective solution and the difficulties associated with accurate diagnosis. Additionally, the fat tissue that often supports the hiatus in obese individuals tends to disappear following bariatric surgery, which can lead to the development or worsening of hiatal hernias post-operatively.

The typical initial approach to treating hiatal hernias involves the use of medication, particularly acid reduction drugs. However, when medication proves ineffective or intolerable, surgical intervention may be necessary. The most common surgical procedure for hiatal hernia repair is called fundoplication. This operation involves tightening the hiatus, often using sutures, and wrapping the upper part of the stomach (fundus) around the lower end of the esophagus. This technique creates an artificial valve mechanism that helps prevent reflux. It should be noted that, for hiatal hernia repairs, there currently is no universal consensus on the use of a sizer (such as a bougie) during hiatal hernia repairs to ensure that the hiatus is not overtightened. This lack of standardization highlights the variability in surgical approaches to this condition.

In some cases, especially when dealing with large hernias, surgeons may opt to use mesh to provide additional support for the hiatal repair. For example, as illustrated in FIG. 1C, a prior art mesh 185 may be positioned around the esophagus 175 at the level of the hiatus 165. This mesh 185 is typically a flat, patterned structure designed to wrap around the esophagus 175 and cover the hiatus 165, providing structural support to the repaired area. While a permanent mesh can be utilized, it is generally not the preferred option. Instead, a bioabsorbable mesh is often favored as it serves as a temporary scaffold that allows the body to generate its own tissue to strengthen the hiatus 165 over time. The placement of the prior art mesh 185, as shown in FIG. 1C, aims to reinforce the weakened area of the diaphragm and help prevent the recurrence of the hiatal hernia by supporting the repaired hiatus 165 and the lower portion of the esophagus 175 where it joins the stomach 170.

Current mesh designs for hiatal hernia repair often include a U-shaped portion intended to support the esophagus, such as the design of the prior art mesh 185 illustrated in FIG. 1C. However, there is a lack of standardization in the installation process, which can lead to inconsistent outcomes. The effectiveness of these prior art meshes in preventing recurrence is not guaranteed, as they primarily provide structural support to the hiatus but do not necessarily prevent the esophagus from sliding back into the chest cavity. This limitation means that even with mesh reinforcement, there remains a risk of hiatal hernia recurrence.

In addition, current standard of care for hiatal hernia repair includes circumferential dissection around the esophagus and upper stomach in order to mobilize the esophagus and stomach out of the chest and reestablish correct positioning of the esophagus in the chest, the gastroesphageal junction at the hiatus, the stomach back in the abdomen, and reestablish the gastric flap valve. This circumferential dissection includes dividing the compromised support structures, such as the phrenoesophageal ligament 168 and the adventitia around the esophagus. Current mesh designs fail to address re-establishment of these support structures, which leaves a significant gap in the current standards of care for hiatal hernia repair.

BRIEF SUMMARY

The present disclosure achieves technical advantages as a hiatal hernia repair mesh with starlock configuration for hiatal hernia repair. In particular embodiments, a hiatal hernia repair mesh may include a mesh frame configured to provide structural support to a repaired hiatus when positioned against the repaired hiatus, and a central opening disposed within the mesh frame. In embodiments, the central opening is configured to surround an esophagus and allow the esophagus to pass through the mesh frame. The hiatal hernia repair mesh also includes a starlock configuration disposed around the central opening that includes a plurality of flexible leaflets extending inwardly from a perimeter of the central opening. Each of the plurality of flexible leaflets may be configured to allow movement of the esophagus in a first direction (e.g., to allow esophageal dilation during peristalsis), while providing resistance against movement of the esophagus toward a chest cavity to prevent recurrence of a hiatal hernia.

In embodiments, the hiatal hernia repair mesh of embodiments may be configured to provide a solution to the challenges associated with hiatal hernia repair. The hiatal hernia repair mesh of embodiments may represent an innovative and unique approach to reinforcing the hiatal area and reestablishing the gastric flap valve, such as after a hiatal hernia repair, and preventing hiatal hernia recurrence. The hiatal hernia repair mesh of embodiments may be configured to offer structural support to the repaired hiatus while also including a unique starlock configuration that may be configured to resist the upward movement of the esophagus (e.g., the movement of the esophagus into the chest cavity), which may operate to prevent hiatal hernia recurrence. The hiatal hernia repair mesh of embodiments may be adaptable to various patient anatomies and surgical techniques, potentially offering a more standardized and effective method for hiatal hernia repair. By combining structural reinforcement with a mechanism to prevent esophageal sliding, the hiatal hernia repair mesh of embodiments may address multiple aspects of hiatal hernia management, potentially improving long-term outcomes for patients undergoing repair procedures.

In embodiments, the hiatal hernia repair mesh of embodiments may address the re-establishment of the support structures, such as the phrenoesophageal ligament that is divided during circumferential dissection, while reinforcing the hiatal hernia repair and positioning the gastroesophageal junction properly at the hiatus allowing the gastric clasp fibers and the gastric sling fibers to be positioned properly to reestablish the gastric flap valve. For example, in embodiments, the flexible leaflets may be configured to provide a structure or scaffolding to enable and guide the re-establishment of the support structures around the esophagus and upper stomach, which may enable the re-establishment of the gastroesophageal flap valve to the proper position to reduce reflux.

It is an object of the disclosure to provide a hiatal hernia repair mesh with starlock configuration for hiatal hernia repair. It is a further object of the disclosure to provide a method of manufacturing a hiatal hernia repair mesh with starlock configuration for hiatal hernia repair. It is still a further object of the disclosure to provide a method of repairing a hiatal hernia using a hiatal hernia repair mesh with starlock configuration.

In one particular embodiment, a hiatal hernia repair mesh with starlock configuration for hiatal hernia repair is provided. The hiatal hernia repair mesh with starlock configuration includes a mesh frame configured to provide structural support to a repaired hiatus when positioned against the repaired hiatus, and a central opening disposed within the mesh frame. In embodiments, the central opening is configured to surround an esophagus and allow the esophagus to pass through the mesh frame. The hiatal hernia repair mesh further includes a starlock configuration disposed around the central opening. In embodiments, the star-lock configuration includes a plurality of flexible leaflets extending inwardly from a perimeter of the central opening, and each of the plurality of flexible leaflets is configured to allow movement of the esophagus in a first direction while providing resistance against movement of the esophagus toward a chest cavity to prevent recurrence of a hiatal hernia.

In another embodiment, a method of manufacturing a hiatal hernia repair mesh with starlock configuration is provided. The method includes forming a mesh frame with a central opening, and creating a starlock configuration around the central opening. In embodiments, the starlock configuration includes a plurality of flexible leaflets. The method also includes positioning the plurality of flexible leaflets to extend inwardly from a perimeter of the central opening, configuring the plurality of flexible leaflets to allow movement of an esophagus in a first direction (e.g., to allow esophageal dilation during peristalsis), while providing resistance against movement of the esophagus toward a chest cavity, and shaping the mesh frame to conform to a hiatus when positioned against the hiatus. In embodiments, the mesh frame is configured to provide structural support to a repaired hiatus.

In yet another embodiment, a method of repairing a hiatal hernia using a hiatal hernia repair mesh with starlock configuration is provided. The method includes repairing a hiatal hernia by suturing one or more portions of a hiatus, and positioning a hiatal hernia repair mesh against the hiatus such that the mesh frame provides structural support to the repaired hiatus. In embodiments, the hiatal hernia repair mesh includes a mesh frame with a central opening and a starlock configuration disposed around the central opening, and the starlock configuration includes a plurality of flexible leaflets extending inwardly from a perimeter of the central opening. The method also includes wrapping the hiatal hernia repair mesh around an esophagus such that the central opening of the mesh frame surrounds the esophagus and the plurality of flexible leaflets of the starlock configuration contact the esophagus and securing the hiatal hernia repair mesh in position. In embodiments, the plurality of flexible leaflets of the starlock configuration are configured to allow movement of the esophagus in a first direction (e.g., to allow esophageal dilation during peristalsis), while providing resistance against movement of the esophagus toward a chest cavity to prevent recurrence of the hiatal hernia. The method further includes securing a fundus of a stomach to a left portion of a diaphragm and the hiatal hernia repair mesh. In embodiments, securing the fundus of the stomach to the left portion of the diaphragm and the hiatal hernia repair mesh facilitates reestablishment of an angle of His and positions gastric clasp fibers and gastric sling fibers in an anatomically correct position to reestablish a competent gastric flap valve.

The foregoing has outlined rather broadly the features and technical advantages of the present disclosure in order that the detailed description of the disclosure that follows may be better understood. Additional features and advantages of the disclosure will be described hereinafter which form the subject of the claims of the disclosure. It should be appreciated by those skilled in the art that the conception and specific embodiment disclosed may be readily utilized as a basis for modifying or designing other structures for carrying out the same purposes of the present disclosure. It should also be realized by those skilled in the art that such equivalent constructions do not depart from the spirit and scope of the disclosure as set forth in the appended claims. The novel features which are believed to be characteristic of the disclosure, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present disclosure.

BRIEF DESCRIPTION OF THE DRAWINGS

For a more complete understanding of the present disclosure, reference is now made to the following descriptions taken in conjunction with the accompanying drawings, in which:

FIG. 5 shows a high-level flow diagram of a method of repairing a hiatal hernia using a hiatal hernia repair mesh with starlock configuration in accordance with embodiments of the present disclosure.

FIG. 6 shows an exemplary flow diagram of operations for manufacturing a hiatal hernia repair mesh with starlock configuration configured with capabilities and functionality for providing structural reinforcement to hiatal hernia repairs and a mechanism to prevent esophageal sliding in accordance with embodiments of the present disclosure.

Figures 1A, 1B, 1C:
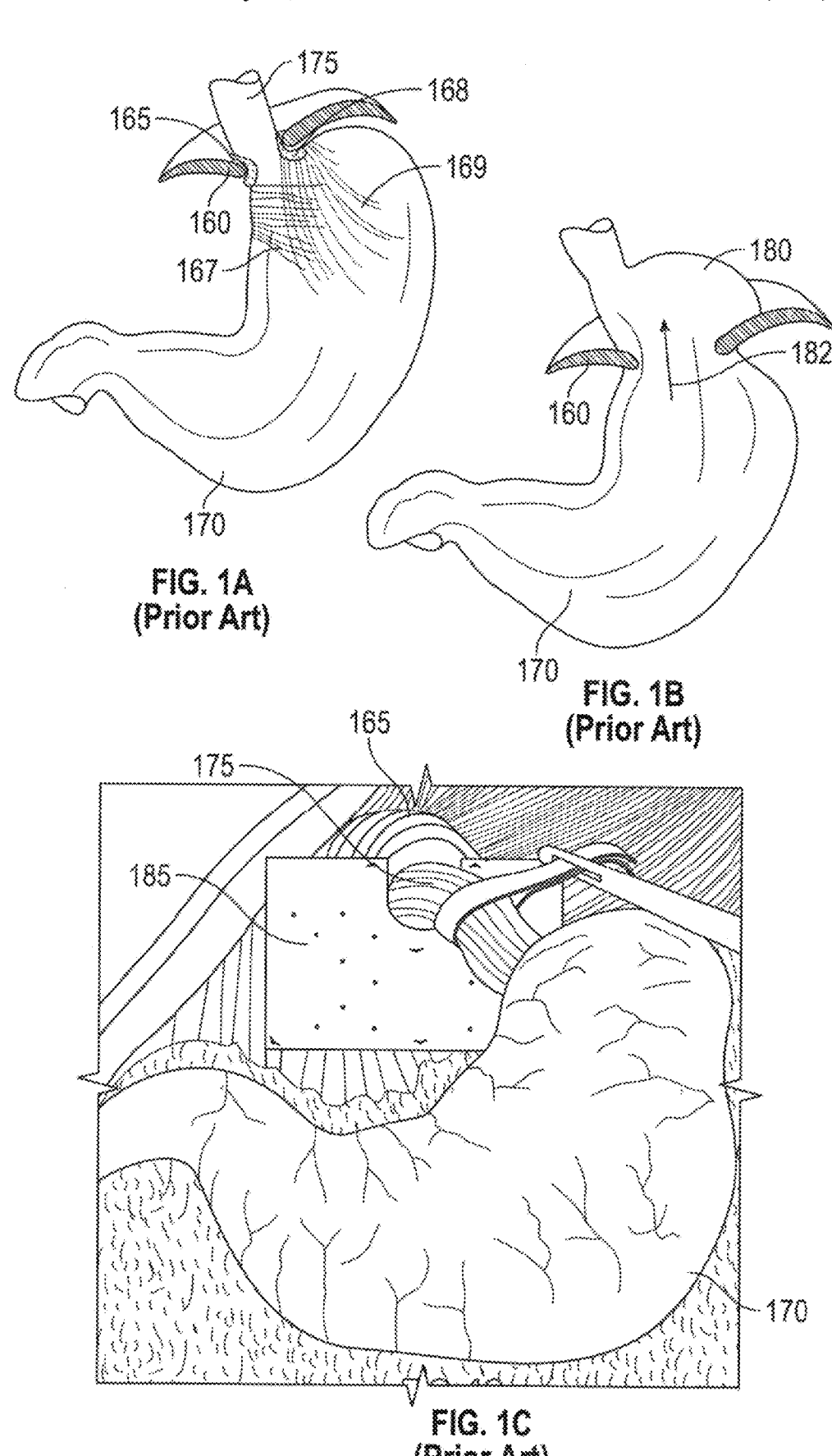
FIG. 1A shows an example of a normal human digestive system.
FIG. 1B shows an example of a hiatal hernia.
FIG. 1C shows an example of a hiatal hernia repair using a prior art mesh.

It should be understood that the drawings are not necessarily to scale and that the disclosed embodiments are sometimes illustrated diagrammatically and in partial views. In certain instances, details which are not necessary for an understanding of the disclosed methods and apparatuses, or which render other details difficult to perceive may have been omitted. It should be understood, of course, that this disclosure is not limited to the particular embodiments illustrated herein.

DETAILED DESCRIPTION

The disclosure presented in the following written description and the various features and advantageous details thereof, are explained more fully with reference to the non-limiting examples included in the accompanying drawings and as detailed in the description. Descriptions of well-known components have been omitted to not unnecessarily obscure the principal features de-scribed herein. The examples used in the following description are intended to facilitate an understanding of the ways in which the disclosure can be implemented and practiced. A person of ordinary skill in the art would read this disclosure to mean that any suitable combination of the functionality or exemplary embodiments below could be combined to achieve the subject matter claimed. The disclosure includes either a representative number of species falling within the scope of the genus or structural features common to the members of the genus so that one of ordinary skill in the art can recognize the members of the genus. Accordingly, these examples should not be construed as limiting the scope of the claims.

A person of ordinary skill in the art would understand that any system claims presented herein encompass all of the elements and limitations disclosed therein, and as such, require that each system claim be viewed as a whole. Any reasonably foreseeable items functionally related to the claims are also relevant. The Examiner, after having obtained a thorough understanding of the disclosure and claims of the present application has searched the prior art as disclosed in patents and other published documents, i.e., nonpatent literature. Therefore, the issuance of this patent is evidence that: the elements and limitations presented in the claims are enabled by the specification and drawings, the issued claims are directed toward patent-eligible subject matter, and the prior art fails to disclose or teach the claims as a whole, such that the issued claims of this patent are patentable under the applicable laws and rules of this country.

Various embodiments of the present disclosure are directed to a hiatal hernia repair mesh with starlock configuration for hiatal hernia repair, methods of manufacturing a hiatal hernia repair mesh with starlock configuration for hiatal hernia repair, and/or methods of repairing a hiatal hernia using a hiatal hernia repair mesh with starlock configuration. In particular embodiments, the hiatal hernia repair mesh may be configured to provide a solution to the challenges associated with hiatal hernia repair. The hiatal hernia repair mesh of embodiments may represent an innovative and unique approach to reinforcing the hiatal area, such as after a hiatal hernia repair, and preventing hiatal hernia recurrence. The hiatal hernia repair mesh of embodiments may be configured to offer structural support to the repaired hiatus while also including a unique starlock configuration that may be configured to resist the upward movement of the esophagus (e.g., the movement of the esophagus into the chest cavity), which may operate to prevent hiatal hernia recurrence and, by reestablishing correct positioning of the esophagus and gastroesophageal junction and stomach relative to the hiatus, allow for reestablishment of the gastric flap valve through correct positioning of the gastric clasp fibers and gastric sling fibers. The hiatal hernia repair mesh of embodiments may be adaptable to various patient anatomies and surgical techniques, potentially offering a more standardized and effective method for hiatal hernia repair. By combining structural reinforcement with a mechanism to prevent esophageal sliding, the hiatal hernia repair mesh of embodiments may address multiple aspects of hiatal hernia management, potentially improving long-term outcomes for patients undergoing repair procedures.

Figures 2A, 2B, 2C:
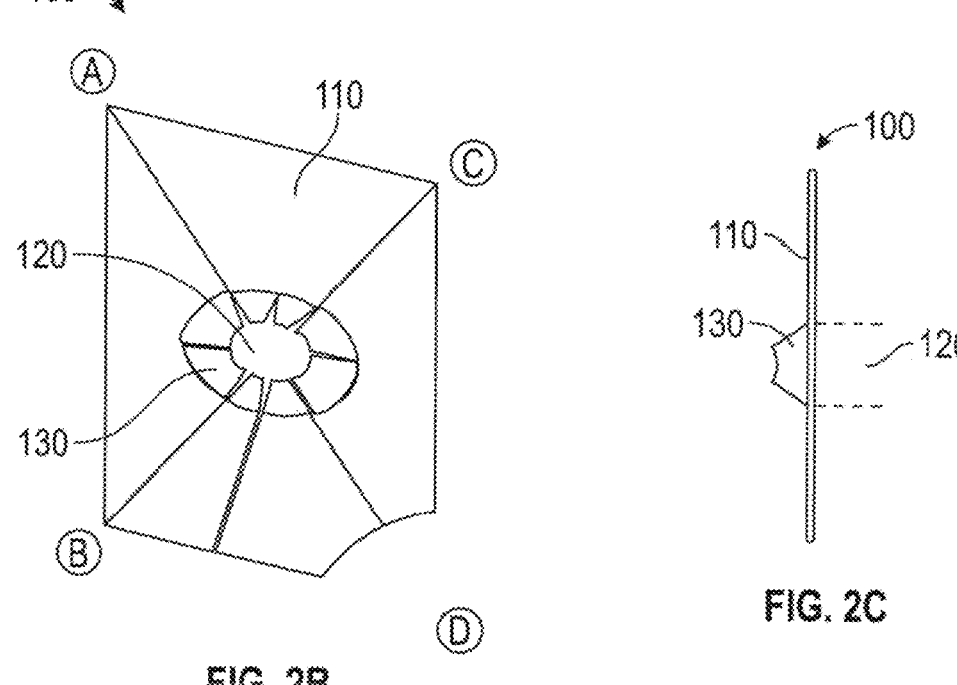
FIG. 2A shows an exemplary hiatal hernia repair mesh with starlock configuration configured with capabilities and functionality for providing structural reinforcement to hiatal hernia repairs and a mechanism to prevent esophageal sliding in accordance with embodiments of the present disclosure.
FIG. 2B shows a perspective view of the hiatal hernia repair mesh with starlock configuration configured with capabilities and functionality for providing structural reinforcement to hiatal hernia repairs and a mechanism to prevent esophageal sliding in accordance with embodiments of the present disclosure.
FIG. 2C shows a side view of the hiatal hernia repair mesh with starlock configuration configured with capabilities and functionality for providing structural reinforcement to hiatal hernia repairs and a mechanism to prevent esophageal sliding in accordance with embodiments of the present disclosure.

FIG. 2A shows an exemplary hiatal hernia repair mesh 100 configured with capabilities and functionality for providing structural reinforcement to hiatal hernia repairs and a mechanism to prevent esophageal sliding in accordance with embodiments of the present disclosure. As shown in the particular embodiment illustrated in FIG. 2A, hiatal hernia repair mesh 100 may include a mesh frame 110, a central opening 120, a starlock configuration 135, a first mesh limb 142, and a second mesh limb 144.

In embodiments, the hiatal hernia repair mesh 100 may be configured to be secured against the diaphragm, for example against the hiatus, to provide structural support to a hiatal hernia repair and to wrap around the esophagus to position a starlock configuration against the esophagus. The starlock configuration may provide resistance against the esophagus movement toward the chest cavity of the hiatus to prevent recurrence of the hiatal hernia. The mesh frame 110 may be designed to conform to the anatomy of the hiatal region, while the central opening 120 may accommodate the passage of the esophagus. The starlock configuration 135 may include a plurality of flexible leaflets that extend inward from the perimeter of the central opening 120, creating a mechanism that allows for normal esophageal function while resisting upward movement (e.g., movement of the esophagus toward the chest cavity).

In some embodiments, the hiatal hernia repair mesh 100 may be used in conjunction with traditional hiatal hernia repair techniques. For example, a hiatal hernia may be initially repaired by suturing one or more of the anterior and posterior portions of the hiatus. The hiatal hernia repair mesh 100 may then be applied to strengthen the hiatal hernia repair and provide an additional mechanism to prevent recurrence. The first mesh limb 142 and second mesh limb 144, separated by the cut line 140, may allow for easy placement of the mesh around the esophagus. Once in position, the starlock configuration 135 may interact with the esophagus, providing a dynamic barrier against upward movement while still allowing for normal digestive function.

The hiatal hernia repair mesh 100 may be constructed from a variety of materials, each selected to provide specific properties that enhance its functionality and effectiveness. In some embodiments, the mesh material may be flexible enough to conform to the anatomical structures while maintaining sufficient structural integrity to provide support for the hiatal hernia repair and to prevent esophageal sliding.

For example, in some embodiments, at least a portion of the hiatal hernia repair mesh 100 may be constructed, made, or manufactures from a woven or non-woven fabric. In some embodiments, a woven structure may be employed, utilizing interlaced fibers or filaments to create a porous yet strong material. In alternative or additional embodiments, at least a portion of the hiatal hernia repair mesh 100 may be constructed using a felt-like material, where fibers are compressed and entangled to form a dense, non-woven structure. These materials may offer varying degrees of flexibility and strength, allowing for customization based on specific patient needs and surgical requirements.

In certain embodiments, the hiatal hernia repair mesh 100 may be made from biocompatible polymers. These biocompatible polymers may include, but are not limited to, polypropylene, polyethylene, polyester, or polytetrafluoroethylene (PTFE). Biocompatible polymers may provide durability and long-term stability in embodiments where hiatal hernia repair mesh 100 may be used as a permanent solution. In other embodiments, the hiatal hernia repair mesh 100 may be made of absorbable or dissolvable materials, such as polylactic acid (PLA), polyglycolic acid (PGA), their copolymers, etc. These biodegradable materials may operate as temporary scaffolds, gradually breaking down as the body's natural tissue regenerates and strengthens the hiatal hernia repair area.

In embodiments, the material used for the hiatal hernia repair mesh 100 may be based on a particular desired interaction between the hiatal hernia repair mesh 100 and the surrounding tissues (e.g., tissues surrounding the hiatal hernia repair area). In some embodiments, the hiatal hernia repair mesh 100 may be coated or impregnated with bioactive substances to promote tissue integration or reduce the risk of infection. For example, antimicrobial agents or growth factors may be incorporated into the hiatal hernia repair mesh 100's structure to enhance its therapeutic potential.

In some embodiments, the starlock configuration 135 and its associated starlock leaflets 130 may be made from the same material as the mesh frame 110, or may be made from a different material, such as a more flexible material to allow for dynamic movement of the starlock leaflets 130. In some embodiments, the starlock leaflets 130 may be constructed from a shape-memory polymer or a material with elastic properties, enabling them to maintain their form and function over time.

In embodiments, the material used for the hiatal hernia repair mesh 100 may be selected based on several factors such as tissue response, potential for adhesion formation, ease of handling during surgical procedures, etc. For example, the material used for the hiatal hernia repair mesh 100 may provide a balance between providing adequate support and minimizing the risk of complications such as erosion or excessive scarring.

In some embodiments, at least a portion of the hiatal hernia repair mesh 100 may be constructed to include self-gripping material. The incorporation of self-gripping material in the construction of the hiatal hernia repair mesh 100 may operate to simplify and streamline the installation process and may potentially eliminate the need for suturing the hiatal hernia repair mesh 100 to the diaphragm. This approach may provide several advantages in terms of ease of use and reduced surgical complexity.

In embodiments, the self-gripping material may be included into the surface of the mesh frame 110 that comes into contact with the diaphragm tissue, such that when the hiatal hernia repair mesh 100 is placed onto the diaphragm to reinforce the hiatal hernia repair area, the self-gripping material makes contact with the diaphragm. In these embodiments, when the hiatal hernia repair mesh 100 is positioned onto the hiatus, the self-gripping surface may adhere to the tissue of the diaphragm or surrounding muscle without the need for traditional sutures. The adhesive properties of the self-gripping material may allow for secure placement of the hiatal hernia repair mesh 100 while potentially reducing the risk of tissue damage associated with suturing.

In practice, a surgeon may position the hiatal hernia repair mesh 100 onto the hiatus and wrap it around the esophagus, ensuring that the central opening 120 is properly aligned. As the mesh is placed against the diaphragm tissue, the self-gripping material may activate, creating a strong bond between the mesh and the surrounding tissue. This adhesion may occur spontaneously, which may reduce the time and complexity of the surgical procedure.

In some embodiments, the self-gripping material may be included onto the surfaces of the first mesh limb 142 and the second mesh limb 144, to extend the self-gripping properties to the interaction between the first mesh limb 142 and the second mesh limb 144. For example, after wrapping the mesh around the esophagus, the surgeon may bring the first mesh limb 142 and the second mesh limb 144 together (e.g., may overlap one mesh limb onto the other one), which may cause the first mesh limb 142 and the second mesh limb 144 to adhere to each other without the need for additional sutures. This functionality may allow for a more streamlined closure of the mesh around the esophagus, potentially improving the overall fit and effectiveness of the hiatal hernia repair procedure.

By potentially eliminating the need for complex suturing techniques, the use of self-gripping material in the hiatal hernia repair mesh 100 may offer fantastic benefits. It may reduce the duration of the surgical procedure, potentially decreasing patient time under anesthesia. Additionally, it may lower the risk of complications associated with suturing, such as tissue tearing or suture breakage. The simplified and streamlined installation process may also contribute to more consistent outcomes across different surgeons and surgical techniques.

It should be noted that while the self-gripping material may provide immediate adhesion, the long-term stability of the mesh may also rely on tissue integration and healing processes. The material properties of the hiatal hernia repair mesh 100 may be configured to promote optimal tissue interaction and incorporation over time, which may lead to a more durable hiatal hernia repair.

In embodiments, incorporating the self-gripping material onto the hiatal hernia repair mesh 100 may include implementing a manufacturing process that modifies the surface characteristics of the hiatal hernia repair mesh 100 material. For example, a process may me implemented for creating a self-gripping hiatal hernia repair mesh that may involve several steps. Initially, the surface of the hiatal hernia repair mesh may be mechanically treated to alter its topography. This treatment may include roughening or abrading the surface, which may result in the partial separation and elevation of individual fibers from the hiatal hernia repair mesh structure. The roughening process may be carefully controlled to ensure that a sufficient number of fibers are affected without compromising the overall integrity of the hiatal hernia repair mesh.

Following the mechanical treatment to elevate the individual fibers of the hiatal hernia repair mesh, the hiatal hernia repair mesh may undergo a thermal processing step. During this phase, heat may be applied to the treated surface, which may cause the exposed fiber ends or tips to undergo a controlled deformation. This deformation may result in the formation of bulbous or mushroom-shaped structures at the tips of the fibers. In embodiments, the heat application may be regulated, such as by an algorithm or machine learning model, to achieve the desired shape and size of these structures without damaging the underlying mesh material.

The resulting surface structure may resemble an array of miniature hooks or mushroom-shaped protrusions. These structures may be configured to interact with the fibrous components of the surrounding tissue, such as the muscle fibers of the diaphragm. When the hiatal hernia repair mesh 100 is placed against the tissue, these mushroom-shaped protrusions may interlock with the tissue fibers, creating a mechanical bond that helps secure the mushroom-shaped protrusions in place.

In embodiments, the self-gripping functionality of the hiatal hernia repair mesh 100 may also facilitate the joining of different parts of the mesh itself. For example, as noted above, when the first mesh limb 142 and the second mesh limb 144 are brought together around the esophagus, their self-gripping surfaces may interact, potentially allowing them to adhere to each other. This self-adhesion property may provide an additional mechanism for securing the mesh in its intended position without relying solely on sutures.

In embodiments, the hiatal hernia repair mesh 100 may include markings 150 on the surface of the hiatal hernia repair mesh 100. In some embodiments, the markings 150 may be configured to assist with proper orientation and placement of the hiatal hernia repair mesh 100 during the hiatal hernia repair procedure. The markings 150 may be represented by dash lines or other visual indicators on the mesh frame 110. In FIG. 2A, markings 150 are represented by dash lines. The markings 150 may operate as guides for the surgeon, helping to ensure accurate positioning of the hiatal hernia repair mesh 100 relative to the anatomical structures involved in the hiatal hernia repair.

In embodiments, the markings 150 may be placed on the mesh frame 110 to correspond with key anatomical landmarks or surgical reference points. For example, certain markings may indicate the anterior, posterior, left, and right orientations of the mesh frame 110 when properly positioned over the hiatus. This may help the surgeon align the hiatal hernia repair mesh 100 correctly with respect to the patient's anatomy, potentially reducing the risk of misalignment or improper placement.

In some embodiments, the markings 150 may include distance indicators or measurement guides. These markings may assist the surgeon in assessing the size and location of the hiatal hernial repair area, which may help the surgeon determine the appropriate positioning for the hiatal hernia repair mesh 100. In particular, the markings 150 may be configured to indicate optimal suture placement locations if sutures are used in conjunction with the hiatal hernia repair mesh 100. These indicators may guide the surgeon in securing the mesh at specific points, which may promote a more standardized and effective fixation technique. In embodiments utilizing self-gripping materials, the markings may highlight areas of enhanced adhesive properties, guiding the surgeon to position these sections against appropriate tissue surfaces for optimal adherence.

In some embodiments, the markings 150 may include indicators specific to the starlock configuration 135. These markings may help ensure proper alignment of the starlock leaflets with the esophagus, potentially optimizing the hiatal hernia repair mesh 100's ability to resist upward movement of the esophagus while allowing for normal digestive function, such as esophageal dilation during peristalsis.

The markings 150 may be applied to the mesh using various techniques that ensure their visibility during the surgical procedure while maintaining the biocompatibility and structural integrity of the mesh. These techniques may include, but are not limited to, printing with biocompatible inks, laser etching, incorporating colored threads or fibers into the mesh structure during the manufacturing process, etc.

In embodiments, the hiatal hernia repair mesh 100 may be configured with a shape that is configured to conform to the anatomical structure of the hiatus and surrounding diaphragm. For example, as shown in FIG. 2A, the mesh frame 110 is depicted as having a diamond or square shape. However, in some embodiments, the shape of the mesh frame 110 may be configured in other geometries, such as circular or oval, depending on the specific requirements of the repair procedure and patient anatomy. In embodiments, the diamond shape of the mesh frame 110 may provide particular advantages in terms of its ability to wrap and conform to the dome-like shape of the hiatus. This diamond-shape configuration may allow for better coverage and support of the repaired area. In some embodiments, the corners of the diamond-shaped mesh may serve specific functions in the placement and securing of the hiatal hernia repair mesh 100.

For example, the top corner of the diamond shape (e.g., corner A in FIG. 2A, which may be positioned at the 12 o'clock position when the hiatal hernia repair mesh 100 is oriented for placement) may be configured to adhere to the apex of the hiatus. This positioning may help anchor the hiatal hernia repair mesh 100 at its uppermost point, providing stability to the overall structure. The side corners of the diamond (e.g., corners B and C, which may be positioned at the 9 o'clock and 3 o'clock positions, respectively) may be configured to adhere to the right and left portions of the diaphragm surrounding the esophagus, from the perspective from the feet of the patient looking toward the head of the patient. These corners may offer additional points of attachment, helping to distribute the supportive force of the hiatal hernia repair mesh 100 evenly around the repaired hiatus. In some embodiments, the bottom corner of the diamond shape (e.g., corner D, which may be positioned at the 6 o'clock position) may feature a curved design rather than a sharp point. This curvature may facilitate easier placement of the mesh under the esophagus, potentially reducing the risk of tissue damage or irritation during the installation process.

In embodiments, the triangular sections formed by the non-curved corners (e.g., corners A, B, and C) may provide structural support to the overall mesh structure. These areas may also serve as optimal locations for suture placement, if sutures are used in the installation process. The geometry of these sections may allow for secure attachment of the hiatal hernia repair mesh 100 to the diaphragm and the hiatal hernia repair are while maintaining the flexibility necessary for the mesh to conform to the patient's anatomy.

In embodiments, the hiatal hernia repair mesh 100 may include a cut line 140 that divides the mesh into two mesh limbs (e.g., first mesh limb 142 and second mesh limb 144). In some embodiments, the cut line 140 may be positioned between corners C and D of the mesh frame 110, typically corresponding to the 6 o'clock and 9 o'clock positions when the mesh is oriented for placement. The placement of this cut line 140 may be carefully considered to optimize the hiatal hernia repair mesh 100's functionality and ease of installation.

In embodiments, the cut line 140 may be configured to allow the hiatal hernia repair mesh 100 to be more easily wrapped around the esophagus during the repair procedure. For example, by separating the hiatal hernia repair mesh 100 into the first mesh limb 142 and the second mesh limb 144, surgeons may have greater flexibility in positioning the hiatal hernia repair mesh 100 around the esophageal structure. For example, when installing the hiatal hernia repair mesh 100, surgeons may separate the first mesh limb 142 and the second mesh limb 144 along the cut line 140. This separation may allow the central opening 120 of the mesh to be carefully positioned around the esophagus, as the second limb 144 may be brought under the esophagus and brought toward the first limb 142. Once properly placed, the first mesh limb 142 and the second mesh limb 144 may be brought back together and secured to the diaphragm and/or to each other.

In some embodiments, the location of the cut line 140 may be configured to facilitate suturing of the mesh to the surrounding muscular tissue. For example, positioning the cut line 140 between the 6 o'clock and 9 o'clock locations may allow for easier access to suturing points at the 6 o'clock and 12 o'clock positions. However, it should be noted that the placement of the cut line 140 may vary depending on specific surgical requirements or patient anatomy. For example, in some embodiments, the position of the cut line 140 may include between corners C and A (corresponding to the 3 o'clock and 12 o'clock positions), between corners A and B (12 o'clock and 9 o'clock), or between corners B and D (9 o'clock and 6 o'clock). In embodiments, the selection of the position of the cut line 140 may be based on factors such as the location of the hiatal hernia repair sutures, the preferred surgical approach, etc.

In some embodiments, the configuration of the hiatal hernia repair mesh 100 may enable one mesh limb to overlap the other when the mesh limbs are brought together. This overlapping configuration may provide additional reinforcement to the repair and may provide more options for securing the mesh in place. For example, the first mesh limb 142 may be positioned to overlap the second mesh limb 144, or vice versa, depending on the specific requirements of the repair procedure. In some embodiments, the overlapping mesh limbs may be sutured together, and in some embodiments may be additionally sutured to the tissue of the diaphragm. The functionality of the hiatal hernia repair mesh 100 to allow the mesh limbs to overlap may contribute to a more customized fit around the esophagus. Surgeons may adjust the degree of overlap to accommodate variations in esophageal diameter or to achieve optimal tension in the placement of the hiatal hernia repair mesh 100.

In embodiments, the hiatal hernia repair mesh 100 may be configured with specific dimensions to accommodate various anatomical configurations and surgical requirements. For example, in some embodiments, the mesh frame 110 may be shaped as a diamond, which can be conceptualized as a square rotated 45 degrees. The side lengths of this square may range from approximately 3 to 8 centimeters, allowing for adaptability to different patient anatomies and hiatal hernia sizes. In embodiments, the central opening 120 of the hiatal hernia repair mesh 100 may have a diameter ranging from about 1 to 4 centimeters before installation. This range of sizes may allow the mesh to accommodate various esophageal diameters while still providing adequate support to the surrounding tissues. It should be noted that the effective size of the central opening 120 may be reduced once the mesh is installed due to the overlapping of the mesh limbs. For example, when the hiatal hernia repair mesh 100 is positioned around the esophagus, the first mesh limb 142 and the second mesh limb 144 may overlap each other. This overlapping configuration may result in a reduction of the central opening 120 diameter by approximately 10-30%. For example, a hiatal hernia repair mesh with an initial central opening diameter of 3 centimeters may have an effective opening of about 2.4 centimeters after installation. This reduction in size may help ensure a snug fit around the esophagus while still allowing for normal esophageal function.

In some embodiments, the reduction in the central opening size due to limb overlap may help ensure that the starlock configuration 135 maintains proper contact with the esophagus, which may enhance its effectiveness in preventing hernia recurrence.

The overall dimensions of the hiatal hernia repair mesh 100, measured from corner to corner along its longest axis, may range from approximately 4 to 12 centimeters. This range of sizes may allow surgeons to select an appropriately sized mesh based on the individual patient's anatomy and the extent of the hiatal defect. The larger sizes may be particularly useful for repairing more extensive hernias or in patients with larger anatomical proportions.

In some embodiments, the dimensions of the hiatal hernia repair mesh 100 may be customizable within the specified ranges. This customization may enable a more tailored approach to hiatal hernia repair, which may improve the fit and effectiveness of the mesh for each individual patient. Surgeons may have the option to select from a range of pre-sized meshes or, in some cases, may be able to trim the mesh to a specific size during the surgical procedure.

In embodiments, the hiatal hernia repair mesh 100 may include a main frame 110 with a central opening 120 disposed approximately in the center of the frame. The central opening 120 may be positioned within about 20% of the frame 110's geometric center. The central opening may be configured to enable the mesh to effectively wrap around the esophagus while providing structural support to the surrounding tissue. In embodiments, the central opening 120 may be configured to accommodate the passage of the esophagus through the hiatal hernia repair mesh 100 and to include a starlock configuration 135 to resist esophageal sliding as described herein.

In some embodiments, the mesh frame 110 of the hiatal hernia repair mesh 100 may be configured to be placed and secured against the hiatus, providing structural support to the hiatal hernia repair. For example, the mesh frame 110 may be made of materials and may have structural properties that allow the mesh frame 110 to withstand the physiological stresses present at the repair site while maintaining its integrity over time. In embodiments, the configuration of the mesh frame 110 may be adaptable to various anatomical variations encountered during hiatal hernia repairs. For example, in some embodiments, the mesh frame 110 may be constructed with a degree of flexibility that allows the mesh frame 110 to conform to the shape of the hiatus, which can vary among patients. This conformability may enable the mesh frame 110 to achieve a more precise fit against the repaired tissue, which may enhance the hiatal hernia repair mesh 100's ability to provide support and to reduce the risk of mesh displacement.

In embodiments, the shape and/or geometry of the mesh frame 110 may be configured to address specific clinical needs or anatomical considerations. In some embodiments, the mesh frame 110 may be configured with a diamond or square shape. In other embodiments, the mesh frame 110 may be configured with a circular shape, which may provide uniform radial support around the hiatus. In some embodiments, the mesh frame 110 may be configured with a rectangular shape, which may be used for cases where additional coverage is desired in certain directions. In some embodiments, the mesh frame 110 may be configured with an oval or elliptical shape, which may be utilized to match the natural contours of some patients' hiatal openings.

It is noted that the shape of the mesh frame 110 may be based on a determination of the distribution of forces across the hiatal hernia repair area. For example, a circular frame may operate to distribute tension more evenly around the circumference of the hiatus, while a rectangular frame might provide enhanced support along its longer axis. The specific geometry selected for the mesh frame 110 may be based on factors such as the size and shape of the hernia, the condition of the surrounding tissue, the surgeon's preference based on the individual patient's needs, etc.

In some embodiments, the mesh frame 110 may include regions of varying rigidity or flexibility. For example, the corners or edges of the frame may be configured with increased rigidity to maintain the overall structure, while the central portions may be more flexible to allow for better conformity to the hiatal anatomy. This differential rigidity may help balance the need for structural support with the requirement for anatomical adaptation.

In embodiments, the surface characteristics of the mesh frame 110 may be configured to enhance the interaction of the mesh frame 110 with the surrounding tissue of the hiatal hernia repair area. For example, in some embodiments, the mesh frame 110 may include a textured surface that promotes tissue ingrowth, which may lead to stronger integration with the hiatal hernia repair area or site over time.

In embodiments, the mesh frame 110 of the hiatal hernia repair mesh 100 may include one or more attachment points configured to provide specific locations where the hiatal hernia repair mesh 100 can be securely fastened to the surrounding anatomical structures, such as the diaphragm, adjacent tissues, and/or surrounding organs. In embodiments, these attachment points may be configured to facilitate secure fixation of the hiatal hernia repair mesh 100. In some embodiments, these attachment points may be reinforced areas of the mesh frame 110, which may feature increased thickness or density of the mesh material. This reinforcement may provide additional strength to withstand the forces applied during suturing or other attachment methods.

In some embodiments, the attachment points may be positioned at key locations on the mesh frame 110, such as at the corners or along the edges. For example, an attachment point at corner A may be utilized to secure the mesh to the anterior portion of the hiatus, while attachment points at corners B and C may be used to anchor the mesh frame 110 to the left and right portions of the diaphragm, respectively, from the perspective of a viewer of the Figures. The specific placement of these attachment points may be optimized to distribute the tension evenly across the mesh and provide maximum support to the repaired area. It is noted that, in embodiments, the attachment point at corner A of the mesh frame 110, which corresponds to the right side of the mesh frame 110 from the perspective of the viewer, may be used to anchor the mesh frame 110 to the left side of the patient, while the attachment point at corner B of the mesh frame 110, which corresponds to the left side of the mesh frame 110 from the perspective of the viewer, may be used to anchor the mesh frame 110 to the right side of the patient. For example, anatomically, point A may be positioned on the left side of the patient and point B may be positioned on the right side of the patient, from a perspective from the patient's feet looking toward the head of the patient.

When sutures are used to secure the hiatal hernia repair mesh 100, the attachment points may operate as locations for suture placement. These attachment points may be configured to withstand the tension of the sutures without compromising the integrity of the hiatal hernia repair mesh 100. In some embodiments, the attachment points may feature pre-marked or pre-punched areas to guide surgeons in optimal suture placement, which may facilitate consistency and effectiveness of the hiatal hernia repair mesh 100's installation process.

In embodiments where self-gripping materials are implemented into the hiatal hernia repair mesh 100, the attachment points may facilitate the mesh's adherence to surrounding tissues. These attachment points may feature an increased surface area of self-gripping material, potentially enhancing the hiatal hernia repair mesh 100's ability to adhere to the diaphragm or other relevant tissues. The self-gripping properties at these attachment points may work in conjunction with the overall self-gripping surface of the mesh to provide thorough and secure attachment. In embodiments, the attachment points may include a specific texture or porosity that promotes the integration of surrounding tissue.

In embodiments, the attachment points may be configured to be adaptable based on individual patient anatomy or specific surgical requirements. For example, some attachment points may be suitable for suturing, while others may be optimized for self-gripping attachment.

In some embodiments, a first attachment point may be disposed at the apex of the mesh frame 110, such as at corner A as illustrated in FIG. 2A. This first attachment point may be configured to secure the hiatal hernia repair mesh 100 to the anterior portion of the hiatus. When viewed from the feet of a patient towards the stomach, this anterior portion would correspond to the top of the hiatus. The positioning of this attachment point may help ensure proper orientation of the hiatal hernia repair mesh 100 and may provide support to the upper region of the repaired area.

In some embodiments, a second attachment point may be located on the left side of the mesh frame 110, such as at corner B. This second attachment point may be configured to secure the hiatal hernia repair mesh 100 to the right portion of the hiatus, from the perspective from the feet of the patient looking toward the head of the patient. In some embodiments, this second attachment point may be positioned under the liver of the patient. In certain surgical scenarios, the weight of the liver itself may be utilized to help maintain the position of the hiatal hernia repair mesh 100. For example, the second attachment point may be placed under the caudate lobe of the liver, allowing the natural weight of the liver to press the hiatal hernia repair mesh 100 corner B against the diaphragm. This approach may reduce the need for sutures at this particular location.

In some embodiments, a third attachment point may be incorporated on the right side of the mesh frame 110, such as at corner C. This third attachment point may be configured to secure the hiatal hernia repair mesh 100 to the left portion of the hiatus, from the perspective from the feet of the patient looking toward the head of the patient. The placement of this attachment point may help ensure balanced tension across the hiatal hernia repair mesh 100 to provide support to the repaired area (e.g., the hiatal hernia repair area or site).

In some embodiments, a fourth attachment point may be positioned on the posterior side of the mesh frame 110, such as at corner D. This fourth attachment point may be configured to secure the hiatal hernia repair mesh 100 to the posterior portion of the hiatus. The inclusion of this posterior attachment point may help complete the circumferential support provided by the hiatal hernia repair mesh 100.

In some embodiments, the specific configurations and characteristics of these attachment points may vary depending on the intended method of fixation. For example, in embodiments utilizing sutures, the attachment points may feature reinforced areas or pre-marked locations to guide optimal suture placement. Alternatively, in configurations implementing self-gripping materials, these attachment points may include enhanced adhesive properties to promote secure attachment to the surrounding tissues.

The central opening 120 may be positioned approximately in the center of the mesh frame 110. In embodiments, the central opening 120 may be configured to allow the esophagus to pass through the hiatal hernia repair mesh 100 when the hiatal hernia repair mesh 100 is installed onto the hiatal hernia repair area. In this manner, the central opening 120 may be configured to enable the hiatal hernia repair mesh 100 to provide structural support and/or reinforcement to the hiatal hernia repair area and the esophagus while allowing the esophagus to pass through the hiatal hernia repair mesh 100.

In embodiments, the central opening 120 may be configured with specific dimensions and characteristics to ensure optimal interaction with the esophagus. For example, in some embodiments, the central opening 120 may be slightly elastic or expandable, allowing the central opening 120 to adapt to the natural movements and variations in esophageal diameter that occur during swallowing and other physiological processes. In some embodiments, this adaptability may be provided by the starlock configuration, as will be described in more detail herein.

In embodiments, the mesh frame 110 surrounding the central opening 120 may be configured to provide structural support to the repaired hiatal area. In some embodiments, the mesh material in proximate to the central opening 120 may be reinforced or may feature a graduated density, which may provide enhanced strength. This reinforcement may help distribute forces evenly and may prevent deformation of the central opening 120 over time.

In some embodiments, the area immediately surrounding the central opening 120 may be textured or treated to promote tissue integration. This may help create a more secure interface between the hiatal hernia repair mesh 100 and the esophagus, which may reduce the risk of mesh migration or hernia recurrence. The texture may be configured to encourage controlled tissue ingrowth without causing excessive adhesion that could impair esophageal function.

In embodiments, the central opening 120 of the hiatal hernia repair mesh 100 may include a starlock configuration 135. In embodiments, the starlock configuration 135 may be configured to address one of the primary challenges in hiatal hernia repair-preventing recurrence. In embodiments, the starlock configuration addresses these issues by providing functionality to resist the upward movement of the esophagus and stomach through the repaired hiatus. In embodiments, the upward movement includes the movement or sliding of the esophagus in the direction of the chest cavity.

In embodiments, the starlock configuration 135 may include a plurality of starlock leaflets 130, as illustrated in FIGS. 2A and 2B. In some embodiments, the plurality of starlock leaflets 130 may be arranged or disposed in a radial pattern around the circumference of the central opening 120. In some embodiments, the starlock leaflets 130 may be fabricated or made from the same material as the mesh frame 110, while in other embodiments, the starlock leaflets 130 may be constructed from a different (e.g., more flexible in some embodiments) material to allow for dynamic movement.

In embodiments, the starlock leaflets 130 of the starlock configuration 135 may be configured to provide unidirectional resistance. For example, each of the starlock leaflets 130 may be configured to allow relatively unrestricted movement of the esophagus in the direction of swallowing (e.g., towards the stomach), while offering significant resistance to movement of the esophagus in the opposite direction (e.g., sliding of the esophagus towards the chest cavity). This functionality of the starlock leaflets 130 may operate to prevent the gastroesophageal (GE) junction, or any other portion of the esophagus, from sliding back into the chest cavity through the hiatus.

For example, the starlock leaflets 130 may be configured with a specific orientation and mechanical properties that are optimized to prevent hiatal hernia recurrence. In embodiments, the starlock leaflets 130 may be slightly bent open, with their free ends oriented towards the abdominal side of the hiatal hernia repair area when installed around the esophagus. This configuration may allow the starlock leaflets 130 to interact dynamically with the esophagus during normal physiological processes. For example, as illustrated in FIGS. 2B and 2C, the starlock leaflets 130 may be configured to extend away from the plane of the mesh frame 110, with their free ends oriented towards the abdominal side of the mesh when installed around the esophagus. FIG. 2B shows an isometric view of the hiatal hernia repair mesh 100, where the starlock leaflets 130 can be seen protruding from the central opening 120 in a radial pattern. FIG. 2C provides a side view, showing the starlock leaflets 130 bent away from the central opening 120 and the plane of the mesh frame 110. This configuration may allow the leaflets 130 to interact dynamically with the esophagus during normal physiological processes, providing resistance against upward movement while allowing for relatively unrestricted downward movement during swallowing.

In embodiments, the starlock leaflets 130 may be configured with a bias towards a closed position. This tendency to return to a more closed state may facilitate resisting upward movement of the esophagus. When the starlock leaflets 130 are bent further open, such as during the passage of food or liquid, the starlock leaflets 130 may exert a gentle force to return to their original position. This property may help ensure that the starlock leaflets 130 maintain consistent contact with the esophageal wall.

As noted above, the starlock leaflets 130 may be configured to allow for unidirectional movement, facilitating normal digestive processes while preventing hernia recurrence. During swallowing, the downward movement of food or liquid through the esophagus may cause the starlock leaflets 130 to bend outwardly, allowing for unimpeded passage. Once the bolus has passed, the starlock leaflets 130 may return to their original position due to their inherent bias.

While the starlock leaflets 130 may be configured to be flexible enough to allow for normal swallowing and esophageal function, the starlock leaflets 130 may also be configured to be sufficiently rigid to effectively grip the esophagus and resist its upward movement (e.g., to resist esophageal sliding toward the chest cavity through the hiatus). For example, the starlock leaflets 130 may be configured to resist the force of the esophagus sliding in the direction toward the chest cavity by receiving the sliding force and providing a resistance against the sliding force. The resistance against the sliding force may be due to the angle of each of the starlock leaflets 130, which may be oriented away from the central opening 120, and/or due to the rigidity of each of the starlock leaflets 130. This orientation may cause the tip of each starlock leaflet 130 to point away from the central opening 120, allowing it to receive the sliding force at an angle.

The rigidity of the starlock leaflets 130 may facilitate preventing the esophageal sliding. As the starlock leaflets 130 are configured with a level of rigidity, the starlock leaflets 130 may not easily bend in response to the sliding force. Instead, the starlock leaflets 130 may maintain their shape and position, effectively preventing the esophagus from sliding into the chest cavity. In embodiments, the rigidity of the leaflets 130 may be calibrated and/or configured to provide sufficient resistance to the sliding force without causing discomfort or impeding normal esophageal function.

In some embodiments, the material properties of the starlock leaflets 130 may be optimized to enhance their resistance to bending. This may involve the use of specific polymers or composite materials that exhibit high flexural strength while maintaining biocompatibility. The thickness and shape of the starlock leaflets 130 may be configured to maximize their resistance to deformation under load.

In some embodiments, the effectiveness of the starlock configuration 135 in preventing esophageal sliding may be enhanced by the collective action of the plurality of starlock leaflets 130. For example, as the esophagus attempts to slide toward the chest cavity, the esophagus may encounter resistance from several starlock leaflets 130 concurrently. This distributed resistance may help to disperse the sliding force over a larger area, which may reduce the stress on individual leaflets and may improve the overall effectiveness of the starlock configuration 135.

In some embodiments, the surface of one or more of the starlock leaflets 130 that comes into contact with the esophageal wall may be configured to enhance the gripping ability of the starlock leaflets 130. This surface treatment may be configured to increase friction between the leaflets 130 and the esophageal wall, which may improve the effectiveness of the starlock configuration 135 in preventing esophageal sliding. For example, in embodiments, the surface of the one or more of the starlock leaflets 130 may be micro-patterned to create a series of small protrusions or indentations. These micro-features may increase the effective surface area of the starlock leaflets 130, which may enhance their ability to grip the esophageal tissue without causing damage or discomfort.

In an embodiment, microneedles may be used on the one or more of the starlock leaflets 130. These microneedles may be very small, such as on the microscale, and may be arranged in a specific pattern across the surface of the one or more of the starlock leaflets 130. The microneedles may be configured to interact with the mucosal layer of the esophagus, providing additional grip without penetrating deeply into the tissue. In some embodiments, the microneedles may be made from biocompatible materials that are sufficiently rigid to maintain their shape but flexible enough to avoid causing tissue damage. The height, spacing, and density of the microneedles may be configured to optimize their gripping effect while ensuring patient safety and comfort.

In some embodiments, enhancing the gripping ability of the starlock leaflets 130 may include may include the use of biocompatible coatings with high-friction properties. These biocompatible coatings may be configured to interact with the esophageal wall to increase the coefficient of friction between the starlock leaflets 130 and the esophageal wall. In some embodiments, these biocompatible coatings may be hydrophilic, allowing them to maintain their gripping properties in the moist environment of the esophagus.

In some embodiments, enhancing the gripping ability of the starlock leaflets 130 may include the use of materials or surface treatments that encourage the growth of tissue over the textured surface, which may create a more natural and stable interface between the leaflets 130 and the esophageal wall that provides gripping ability. In some embodiments, multiple approaches for enhancing the gripping ability of the starlock leaflets 130 may be used. For example, a micro-textured surface may be combined with a high-friction coating, or microneedles may be interspersed with areas of different surface treatments.

In embodiments, the tips or ends of each of the starlock leaflets 130 may be configured with a shape configured to optimize the gripping ability of the starlock leaflets 130 on the esophageal wall. In some embodiments, rather than having sharp, pointed ends, the tips of the starlock leaflets 130 may be cut or shaped to create a broader surface area for contact with the esophagus. This configuration may enhance the starlock leaflets 130's ability to maintain a secure grip on the esophageal tissue.

In some embodiments, the cut or shaped tips of the leaflets 130 may take various forms, depending on the specific requirements of the hiatal hernia repair mesh 100. In some embodiments, the tips may be flattened or slightly rounded, creating a small platform at the end of each starlock leaflet 130. This platform may increase the contact area between the leaflet and the esophageal wall, which may help to distribute the gripping force of the starlock leaflets over a larger surface of the esophageal wall and may reduce the risk of localized pressure points.

In some embodiments, the tips of the starlock leaflets 130 may be configured with a slight concave curvature. This curvature may allow the leaflet tips to conform more closely to the natural curvature of the esophageal wall, which may help to increase the contact area and improve the overall grip. The concave shape may also help to cradle the esophageal tissue, providing a more secure hold without the need for sharp or pointed edges.

In some embodiments, the tips of one or more of the starlock leaflets 130 may be made from a slightly softer or more compliant material than the rest of the starlock leaflet, allowing them to adapt to small variations in the esophageal surface while still maintaining their overall structural integrity. In some embodiments, the cut or shaped tips of the leaflets 130 may incorporate micro-texturing or surface treatments to further enhance their gripping capabilities. These surface modifications may work in conjunction with the broader contact area to provide an enhanced approach to preventing esophageal sliding.

In some embodiments, the number of starlock leaflets 130 in the starlock configuration 135 of the hiatal hernia repair mesh 100 may vary to accommodate different anatomical requirements and surgical preferences, which may allow for customization of the hiatal hernia repair mesh 100 to suit individual patient needs and specific repair scenarios. In embodiments, the number of starlock leaflets 130 in the starlock configuration 135 may range from a single leaflet to sixteen or more. In some embodiments, a configuration with fewer leaflets may be preferred for smaller hiatal defects or in cases where minimal intervention is desired. Conversely, a higher number of leaflets may be utilized for larger hernias or in situations where more support is appropriate.

In embodiments, a single-leaflet configuration may provide the benefit of simpler manufacturing and installation while still providing a basic level of resistance against esophageal sliding. In contrast, configurations with multiple leaflets may provide more distributed support and more uniform pressure distribution around the esophageal circumference. In some embodiments, the number of starlock leaflets 130 may be determined based on the diameter of the central opening 120 and/or the desired level of coverage around the esophagus. Larger central openings may accommodate a higher number of leaflets, while smaller openings may be better suited to fewer leaflets to avoid overcrowding.

In some embodiments, the starlock configuration 135 may feature an even number of starlock leaflets 130, such as four, six, eight, or twelve. This symmetrical configuration may contribute to balanced force distribution and may simplify the manufacturing process. Odd numbers of starlock leaflets may be used in certain configurations to achieve specific functional outcomes or to address particular anatomical considerations.

In embodiments, the starlock leaflets number may be used to manage or control the overall flexibility and adaptability of the starlock configuration 135. For example, a higher number of starlock leaflets may be used for finer adjustments to esophageal movements, which may provide a more nuanced response to physiological processes such as swallowing. Conversely, fewer starlock leaflets may be used to provide more robust resistance, even if with potentially less granular adaptation to esophageal dynamics.

In embodiments, the material properties and dimensions of individual starlock leaflets 130 may be adjusted based on their number within the starlock configuration 135. For instance, in configurations with fewer starlock leaflets, each starlock leaflet may be made slightly larger or more rigid to compensate for the reduced total number. Conversely, configurations with many starlock leaflets may utilize thinner or more flexible individual components to maintain overall comfort and functionality.

Figures 3A, 3B:
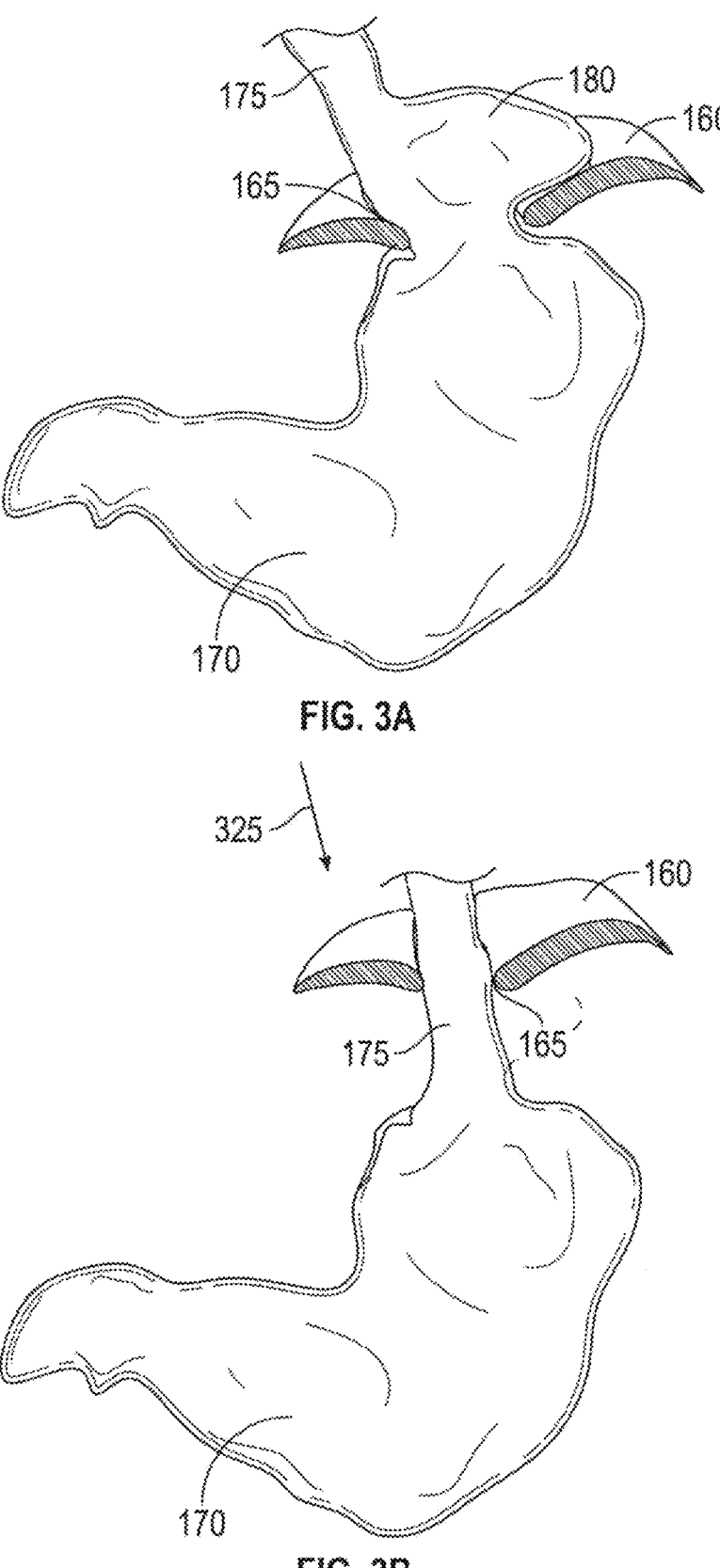
FIGS. 3A-3C illustrate a progression of a hiatal hernia repair procedure in accordance with embodiments of the present disclosure.
Figure 3C:
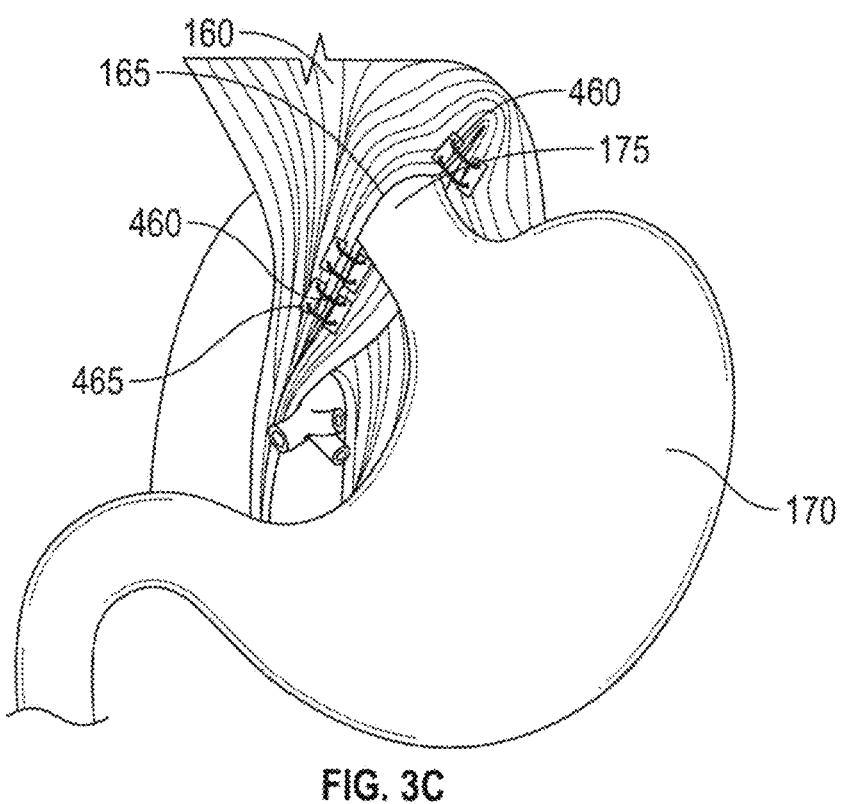
Figure 4A:
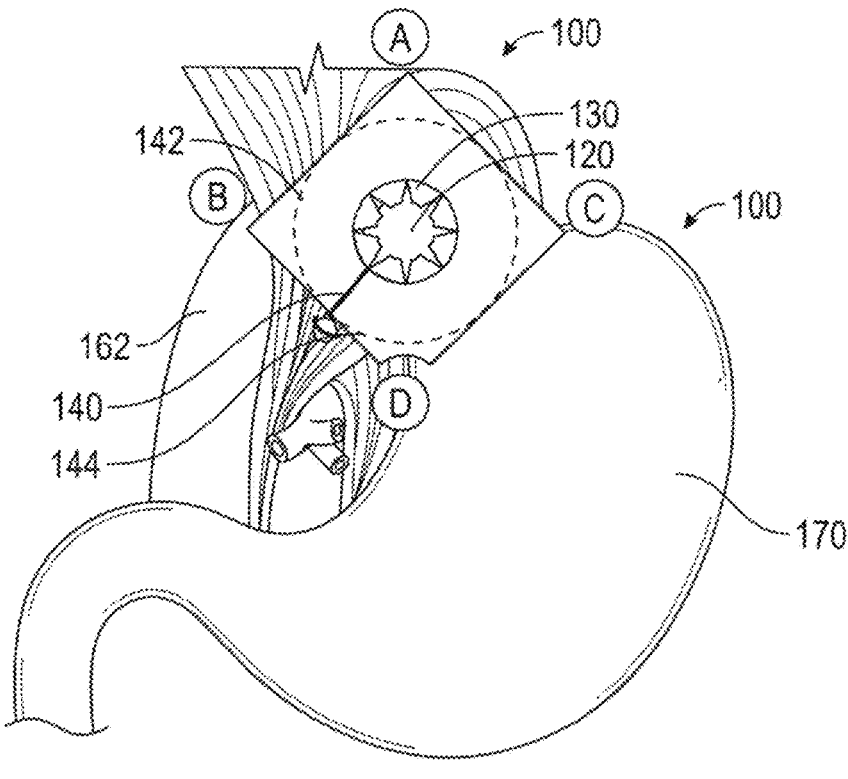
FIGS. 4A-4C illustrate a progression of a procedure for reinforcing or supporting the hiatal hernia repair using a hiatal hernia repair mesh with starlock configuration configured with capabilities and functionality in accordance with embodiments of the present disclosure.
Figure 4B:
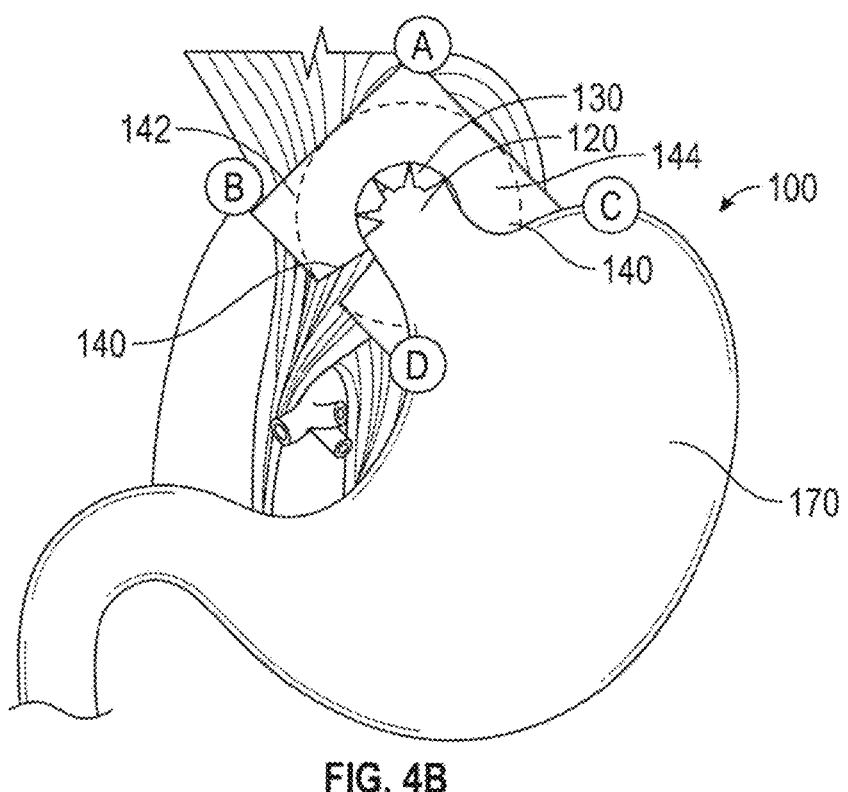
Figure 4C:
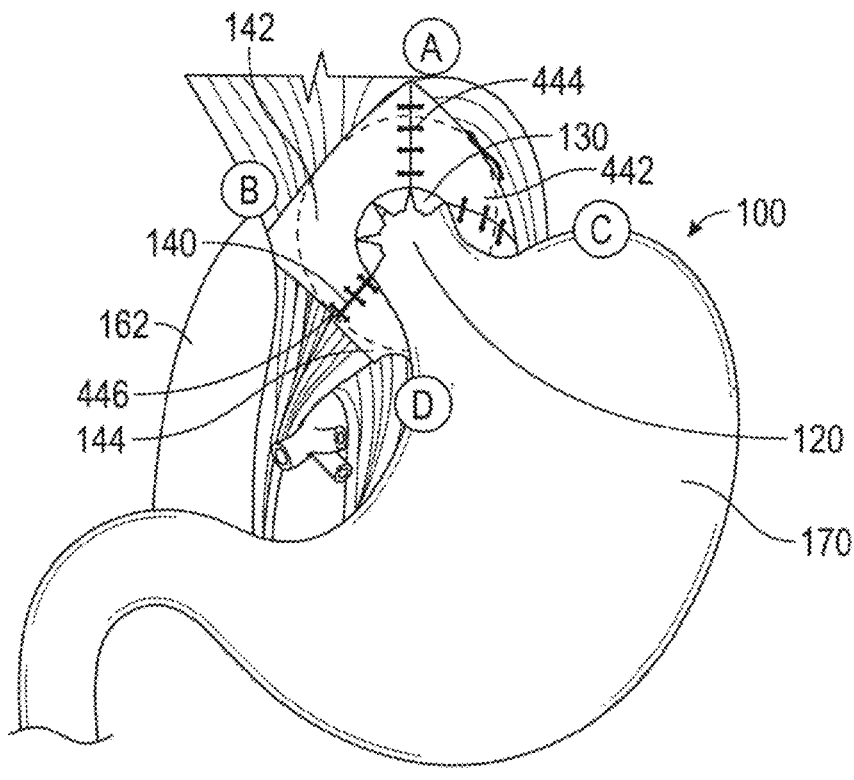

Operation of a hiatal hernia repair mesh 100 for reinforcing or supporting a hiatal hernia repair will now be discussed with respect to FIG. 5, as well as FIGS. 3A-3C and 4A-4C, in accordance with embodiments of the present disclosure. FIG. 5 shows a high-level flow diagram of a method 500 of repairing a hiatal hernia using a hiatal hernia repair mesh with starlock configuration in accordance with embodiments of the present disclosure. FIGS. 3A-3C illustrate the progression of a typical hiatal hernia repair procedure. FIGS. 4A-4C illustrate the progression of a procedure for reinforcing or supporting the hiatal hernia repair (e.g., the hiatal hernia repair illustrated in FIGS. 3A-3C) using a hiatal hernia repair mesh (e.g., hiatal hernia repair mesh 100 as illustrated in FIGS. 2A-2C).

At block 502, a hiatal hernia repair procedure is performed. In embodiments, this procedure may begin with the identification and assessment of the hiatal hernia, as illustrated in FIG. 3A. In this example, the hiatal hernia 180 may be characterized by a portion of the stomach protruding through an enlarged hiatus 165 in the diaphragm 160 into the chest cavity. The hiatal hernia repair procedure may include several steps to restore the normal anatomical configuration. In some embodiments, the first step may include repositioning the esophagus 175 and stomach 170 to their proper locations. This may include carefully manipulating the gastroesophageal (GE) junction, moving it back into its correct position below the diaphragm, as illustrated in FIG. 3B.

Once the esophagus and stomach are properly positioned, the hiatal hernia repair procedure may include addressing the enlarged hiatus. In some embodiments, this may include using sutures to tighten and reinforce the hiatal opening. As shown in FIG. 3C, sutures may be placed along the anterior side and posterior side of the hiatus to reduce its size and provide support. However, it should be noted that the suturing technique may vary depending on the specific case and surgeon preference. In some procedures, sutures may be placed only on the posterior side or anterior side of the hiatus. The suturing process, represented by the sutures of the hiatal hernia repair 460 in FIG. 3C, may be performed using various techniques and materials. In some cases, non-absorbable sutures may be used to provide long-term support, while in others, absorbable sutures may be preferred. The number, placement, and tension of the sutures may be determined based on the size of the hernia, the condition of the surrounding tissue, the individual patient's anatomy, etc.

In some embodiments, the hiatal hernia repair procedure may include the use of pledgets 465, such as felt pledgets, in conjunction with the sutures. These pledgets 465 may be used to reinforce the suture lines and distribute the tension over a larger area of tissue, which may operate to reduce the risk of suture pull-through and enhance the overall strength of the repair. It is noted that although FIG. 3C illustrates the use of pledgets 465 in the posterior repair, it should be understood that pledgets may be incorporated both posteriorly and anteriorly in some embodiments. The inclusion of pledgets may provide additional support to the repaired hiatus, particularly in cases where the surrounding tissue may be weakened or thinned. The size, shape, and material of the pledgets 465 may be selected based on the specific requirements of the repair and the surgeon's preference.

In some embodiments, the repair procedure may also involve additional steps to reinforce the area and prevent recurrence. This may include the mobilization of surrounding tissues, such as the fundus of the stomach, to provide extra support to the repaired hiatus. In certain cases, the procedure may also involve the creation of a fundoplication, where the upper part of the stomach is wrapped around the lower esophagus to create an additional barrier against reflux.

At block 504, the hiatal hernia repair mesh 100 may be positioned against the hiatus to provide structural support to the repaired area. As illustrated in FIG. 4A, the hiatal hernia repair mesh 100 may be placed over the hiatus, with the mesh frame 110 configured to conform to the anatomical contours of the surrounding diaphragmatic tissue. The hiatal hernia repair mesh 100 may include the central opening 120, which may be aligned with the esophagus to allow for its passage through the hiatal hernia repair mesh 100. Surrounding the central opening 120, the mesh may include a starlock configuration 135, comprising a plurality of flexible leaflets (e.g., starlock leaflets 130) that extend inwardly from the perimeter of the central opening 120.

In some embodiments, the positioning of the hiatal hernia repair mesh 100 may be guided by anatomical landmarks.

For example, the mesh frame 110 may be oriented such that its corners align with specific points on the diaphragm. As shown in FIG. 4A, corner A of the mesh may be positioned towards the anterior portion of the hiatus, while corners B and C may be aligned with the left and right aspects of the diaphragm, respectively. In embodiments, as the hiatal hernia repair mesh 100 is positioned, the flexible leaflets (e., the starlock leaflets 130) of the starlock configuration 135 may be oriented to extend towards the esophagus. This arrangement may allow the flexible leaflets to interact with the esophageal wall, providing a dynamic support mechanism that adapts to esophageal movements while resisting upward displacement.

In some embodiments, the placement of the hiatal hernia repair mesh 100 may take into account the surrounding anatomical structures. For example, as illustrated in FIG. 4A, the positioning of the hiatal hernia repair mesh 100 may consider the proximity of the liver 162. The hiatal hernia repair mesh 100 may be placed in such a way that it does not interfere with the natural position of the liver while still providing optimal coverage of the hiatal area.

At block 506, the hiatal hernia repair mesh 100 may be wrapped around the esophagus. As illustrated in FIG. 4B, the mesh frame 110 may be carefully maneuvered to encircle the esophagus, ensuring that the central opening 120 of the mesh frame surrounds the esophageal passage. In some embodiments, the hiatal hernia repair mesh 100 may include a cut line 140 that defines two distinct mesh limbs: the first mesh limb 142 and the second mesh limb 144. This feature may allow for easier manipulation and placement of the hiatal hernia repair mesh 100 around the esophagus. For example, during the wrapping process, the first mesh limb 142 and the second mesh limb 144 may be separated, causing the central opening 120 to enlarge and enabling the surgeon to position the central opening 120 around the esophagus with greater precision and control.

As the hiatal hernia repair mesh 100 is wrapped around the esophagus, the plurality of flexible leaflets (e.g., the plurality of starlock leaflets 130) that form the starlock configuration 135 may come into contact with the esophageal wall. This contact may allow the flexible leaflets to provide dynamic support and resistance against upward movement of the esophagus toward the chest cavity.

In embodiments, the mesh frame 110 may be positioned against the diaphragm, covering the area where the sutures of the hiatal hernia repair 460 were previously placed. This placement may operate to reinforce the initial repair, providing an additional layer of support to the weakened hiatal region. The conforming nature of the mesh frame 110 may allow the mesh frame 110 to adapt to the contours of the diaphragm, ensuring a secure fit and coverage of the hiatal hernia repair 460.

At block 508, the hiatal hernia repair mesh 100 may be secured in position to provide support to the hiatal hernia repair and prevent recurrence of the hiatal hernia. As illustrated in FIG. 4C, the hiatal hernia repair mesh 100 may be fixed in place using various techniques. For example, in some embodiments, sutures may be used to anchor the hiatal hernia repair mesh 100 to the surrounding tissue. For example, a first suture 444 may be placed at corner A of the hiatal hernia repair mesh 100, securing it to the anterior portion of the hiatus. A second suture 442 may be positioned at corner C, attaching the hiatal hernia repair mesh 100 to the right side of the diaphragm. The left side of the hiatal hernia repair mesh 100, particularly corner B, may be positioned under the liver 162. The natural weight of the liver may help maintain the position of the hiatal hernia repair mesh 100 in this area, without the need for sutures or additional fixation at this point.

In embodiments, the third sutures 446 may be used to attach the first mesh limb 142 to the second mesh limb 144, as well as to secure the first mesh limb 142 and the second mesh limb 144 to the diaphragm. For example, one of the mesh limbs may be positioned to overlap the other mesh limbs, and the third sutures 446 may be placed through this overlapping region to join the mesh limbs together. This overlapping configuration may provide additional reinforcement to the repair site. Concurrently, these same third sutures 446 may penetrate through both mesh limbs and into the underlying diaphragmatic tissue, effectively anchoring the overlapping region to the repaired hiatus.

In some embodiments, the hiatal hernia repair mesh 100 may include self-gripping materials, which may operate to reduce or eliminate the need for sutures. These self-gripping properties may allow the mesh to adhere securely to the surrounding tissues.

In embodiments, the plurality of flexible leaflets forming the starlock configuration 135 may operate to prevent hiatal hernia recurrence. These flexible leaflets may be configured to allow movement of the esophagus in the direction of normal swallowing (e.g., towards the stomach) while providing resistance against movement of the esophagus towards the chest cavity. This unidirectional flexibility may operate to maintain normal esophageal function while preventing the upward sliding of the esophagus into the chest cavity that may lead to hiatal hernia recurrence.

In some embodiments, the resistance provided by the starlock leaflets 130 may be enhanced by their orientation and material properties. For example, the starlock leaflets 130 may be angled or curved in such a way that they easily flex outward when the esophagus moves downward but catch and resist any upward movement.

In embodiments, the starlock leaflets 130 may be configured to facilitate re-establishment of the support structures of the gastroesophageal junction, such as the phrenoesophageal ligament and to correctly position the gastric clasp fibers and the gastric sling fibers. For example, the starlock leaflets 130 may provide a scaffolding to enable the re-establishment of the support structures of the gastroesophageal junction. The configuration and placement of the starlock leaflets 130 may create a supportive framework around the esophagus that may guide the natural healing process and tissue regeneration. As the starlock leaflets 130 extend inwardly from the perimeter of the central opening, they may form a three-dimensional structure that mimics the natural anatomical arrangement of these support structures.

For example, the phrenoesophageal ligament, which normally anchors the esophagus to the diaphragm, may be dissected during the hiatal hernia repair. In embodiments, the starlock leaflets 130 may provide a temporary substitute for this ligament's function. As tissue healing progresses, the starlock leaflets 130, which may be made of a bioabsorbable material, may serve as a guide for the regeneration of the phrenoesophageal ligament, and/or may promote the growth of new connective tissue along their surfaces. This may help to re-establish a strong connection between the esophagus and the diaphragm.

In some embodiments, the gastric sling fibers and gastric clasp fibers, which may provide further support for the lower esophageal sphincter, may be malpositioned in a hiatal hernia and may be repositioned correctly during the hiatal hernia repair. In embodiments, the starlock leaflets 130 may provide correct positioning of these support fibers while the body heals after repair allowing for reestablishment of a competent gastric flap valve. In embodiments, the starlock leaflets 130 may also provide scaffolding functionality for the gastric sling fibers. In embodiments, the orientation and flexibility of the starlock leaflets 130 may allow them to interact with the upper portion of the stomach in a way that encourages the regrowth and reattachment of these important muscular fibers. As the phrenoesophageal ligament regenerates, and as the starlock leaflets 130 are dissolved or absorbed, the starlock leaflets 130 may integrate with the esophagus and stomach to provide a support structure for the gastroesophageal junction and reestablishment of a functional gastric flap valve.

In some embodiments, the material properties of the starlock leaflets 130 may be optimized to enhance their scaffolding functionality. For example, the surface of the starlock leaflets 130 may be treated or textured in a way that promotes cell adhesion and tissue ingrowth. This may facilitate the attachment and proliferation of fibroblasts and other cells involved in tissue repair and regeneration. In some embodiments, the porosity of the starlock leaflets 130 may be configured to allow for nutrient exchange and vascularization, which may facilitate integration of the regenerated support structures.

In some alternative or additional embodiments, method 500 may include securing a fundus of a stomach to a left portion of a diaphragm and the hiatal hernia repair mesh. For example, securing the fundus, which may include the upper portion of the stomach closest to the esophagus, may include positioning the fundus into the position against the left portion of the diaphragm and the hiatal hernia repair mesh and then securing the fundus to the left portion of the diaphragm and the hiatal hernia repair mesh. In embodiments, the fundus may be secured using various methods, which may include sutures to anchor the fundus to the diaphragm and hiatal hernia repair mesh, surgical staples, or biocompatible adhesives, etc.

In embodiments, securing the fundus to the left portion of the diaphragm and the hiatal hernia repair mesh may facilitate several features and/or functions. For example, the angle of His, which may include the angle formed between the esophagus and the fundus of the stomach, may be reestablished or restored to its normal anatomical configuration, which may help with preventing reflux. Additionally, or alternatively, by securing the fundus to the left portion of the diaphragm and the hiatal hernia repair mesh, the gastric clasp fibers and gastric sling fibers may be guided into their anatomically correct positions, which may contribute to the correct operation of the lower esophageal sphincter and/or a component gastric flap valve. A correct positioning of the fundus and associated structures may facilitate reestablishment of a functional gastric flap valve.

FIG. 6 shows an exemplary flow diagram of operations 600 for manufacturing a hiatal hernia repair mesh with starlock configuration for hiatal hernia repair in accordance with embodiments of the present disclosure. For example, the steps illustrated in the example blocks shown in FIG. 6 may be performed to manufacture hiatal hernia repair mesh 100 of FIGS. 1-4C, according to embodiments herein.

At block 602, a mesh frame with a central opening is formed. For example, a mesh frame (e.g., the mesh frame 110 of FIG. 2A) may be formed with a central opening (e.g., the central opening 120 of FIG. 2A). In some embodiments, the mesh frame may be constructed from a biocompatible material such as polypropylene, polyester, or a combination of materials. The central opening may be sized to accommodate the passage of an esophagus while providing sufficient surrounding material for structural support.

At block 604, a starlock configuration is created around the central opening. For example, a starlock configuration (e.g., starlock configuration 135 of FIG. 2A) is created around the central opening (e.g., the central opening 120 of FIG. 2A). In embodiments, the starlock configuration may include a plurality of flexible leaflets (e.g., the starlock leaflets 130 of FIG. 2A) arranged in a radial pattern around the perimeter of the central opening. These leaflets may be formed integrally with the mesh frame or may be attached as separate components. The number and size of the leaflets may vary depending on the specific requirements of the hiatal hernia repair.

At block 606, the flexible leaflets are positioned to extend inwardly from the perimeter of the central opening. In embodiments, the inward orientation of the flexible leaflets may allow the flexible leaflets to interact with the esophagus when the mesh is in place. The positioning of the leaflets may be achieved during the manufacturing process or may be adjustable by the surgeon during the implantation procedure.

At block 608, the flexible leaflets are configured to allow movement of the esophagus in a first direction while providing resistance against movement of the esophagus toward the chest cavity. In embodiments, this configuration of the flexible leaflets to resist movement of the esophagus toward the chest cavity may include a combination of the material properties, geometry, and shape of the leaflets to obtain the desired flexibility and resistance. For example, the flexible leaflets may be slightly bent outwardly (e.g., may be bent at an angle away from the plane of the mesh frame) and/or may be configured with a slight curve or angle that allows them to bend easily in one direction but stiffen when force is applied in the opposite direction.

At block 610, the mesh frame is shaped to conform to the hiatus when positioned against it. In embodiments, the shaping of the mesh frame may include creating a specific contour or curvature in the mesh frame that matches the anatomical structure of the hiatus. The shaped mesh frame may be configured to provide optimal structural support to the repaired hiatus. In some embodiments, the shaping of the mesh frame may be pre-formed during manufacturing, while in others, it may be adjustable by the surgeon to accommodate individual patient anatomy.

Although the present disclosure and its advantages have been described in detail, it should be understood that various changes, substitutions, and alterations can be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

Moreover, the description in this patent document should not be read as implying that any particular element, step, or function can be an essential or critical element that must be included in the claim scope. Also, none of the claims can be intended to invoke 35 U.S.C. § 112(f) with respect to any of the appended claims or claim elements unless the exact words "means for" or "step for" are explicitly used in the particular claim, followed by a participle phrase identifying a function. Use of terms such as (but not limited to) "mechanism," "module," "device," "unit," "component," "element," "member," "apparatus," "machine," "system," "processor," "processing device," or "controller" within a claim can be understood and intended to refer to structures known to those skilled in the relevant art, as further modified or enhanced by the features of the claims themselves, and can be not intended to invoke 35 U.S.C. § 112(f). Even under the broadest reasonable interpretation, in light of this paragraph of this specification, the claims are not intended to invoke 35 U.S.C. § 112(f) absent the specific language described above.

The disclosure may be embodied in other specific forms without departing from the spirit or essential characteristics thereof. For example, each of the new structures described herein, may be modified to suit particular local variations or requirements while retaining their basic configurations or structural relationships with each other or while performing the same or similar functions described herein. The present embodiments are therefore to be considered in all respects as illustrative and not restrictive. Accordingly, the scope of the disclosures can be established by the appended claims rather than by the foregoing description. All changes which come within the meaning and range of equivalency of the claims are therefore intended to be embraced therein. Further, the individual elements of the claims are not well-understood, routine, or conventional. Instead, the claims are directed to the unconventional inventive concept described in the specification.

What is claimed is:

1. A method of repairing a hiatal hernia, comprising:

repairing a hiatal hernia by suturing one or more portions of a hiatus;

positioning a hiatal hernia repair mesh against the hiatus such that the mesh frame provides structural support to the repaired hiatus, wherein the hiatal hernia repair mesh includes a mesh frame with a central opening and a starlock configuration disposed around the central opening, wherein the starlock configuration includes a plurality of flexible leaflets extending inwardly from a perimeter of the central opening;

wrapping the hiatal hernia repair mesh around an esophagus such that the central opening of the mesh frame surrounds the esophagus and the plurality of flexible leaflets of the starlock configuration contact the esophagus;

securing the hiatal hernia repair mesh in position, wherein the plurality of flexible leaflets of the starlock configuration are configured to allow movement of the esophagus in a first direction to allow esophageal dilation during peristalsis while providing resistance against movement of the esophagus toward a chest cavity to prevent recurrence of the hiatal hernia; and securing a fundus of a stomach to a left portion of a diaphragm and the hiatal hernia repair mesh, wherein securing the fundus of the stomach to the left portion of the diaphragm and the hiatal hernia repair mesh facilitates reestablishment of an angle of His and positions gastric clasp fibers and gastric sling fibers in an anatomically correct position to reestablish a competent gastric flap valve.

2. The method of claim 1, wherein the hiatal hernia repair mesh has a diamond shape with four corners.

3. The method of claim 2, wherein positioning the hiatal hernia repair mesh includes aligning one of the corners with an anterior portion of the hiatus, wherein the corner aligned with the anterior portion of the hiatus has a rounded or truncated shape.

4. The method of claim 1, wherein the plurality of flexible leaflets have sufficient rigidity to resist a sliding force of the esophagus toward the chest cavity.

5. The method of claim 1, wherein tips of one or more of the plurality of flexible leaflets have a non-pointed shape to provide increased surface area for contacting an esophageal wall.

6. The method of claim 5, wherein the tips of the one or more of the plurality of flexible leaflets include a gripping surface configured to enhance contact with the esophageal wall.

7. The method of claim 1, wherein the plurality of flexible leaflets are oriented at an angle away from the central opening.

8. The method of claim 1, wherein wrapping the hiatal hernia repair mesh around the esophagus includes separating a first mesh limb from a second mesh limb along a cut line extending from the central opening to an outer edge of the mesh frame.

\* \* \* \* \*